United States Patent [19]

Morris et al.

[11] Patent Number: 4,813,927
[45] Date of Patent: Mar. 21, 1989

[54] PARALLEL INFUSION APPARATUS AND METHOD

[75] Inventors: Robert E. Morris; Clark D. Witherspoon, both of Birmingham; William E. Goggans, Jr., Pinson, all of Ala.

[73] Assignee: Vitreoretinal Development, Inc., Birmingham, Ala.

[21] Appl. No.: 99,533

[22] Filed: Sep. 22, 1987

[51] Int. Cl.<sup>4</sup> ............................................. A61M 37/00
[52] U.S. Cl. ........................................ 604/23; 604/28; 604/48; 604/141
[58] Field of Search ..................... 604/22–24, 604/26–28, 118, 119, 48, 49, 141–148; 433/98, 101

[56]  References Cited
U.S. PATENT DOCUMENTS 4,509,507  4/1985  Yabe .......................................... 604/27

FOREIGN PATENT DOCUMENTS 50507  12/1940  France .................................. 604/26

OTHER PUBLICATIONS

"Automated Regulation of Fluid Infusion Pressure During Vitrectomy", Witherspoon, M. D. et al., Arch of Opthalmology, vol. 104, p. 1551, Oct. 1986.

Primary Examiner—C. Fred Rosenbaum
Assistant Examiner—J. L. Kruter
Attorney, Agent, or Firm—Jennings, Carter, Thompson & Veal

[57]  ABSTRACT

Apparatus for us in intraocular surgical procedures utilizes a plurality of flexible conduits and a control valve to selectively supply an infusion cannula with either fluid or air. The air and fluid are pressurized for infusion by a continuous infusion air pump and supplied to the valve by parallel lengths of flexible tubing. The apparatus may be used to monitor and control the infusion pressure or to switch the infusion agent in a minimal time.

20 Claims, 1 Drawing Sheet

PARALLEL INFUSION APPARATUS AND METHOD

FIELD OF THE INVENTION

The present invention relates generally to apparatus and methods used in surgery conducted on the retina and vitreous portions of the eye. More particularly, the present invention relates to apparatus used in continuous infusion processes associated with such surgery. In even greater particularity, the present invention relates to apparatus for rapidly converting between fluid and air infusion during such surgery.

BACKGROUND OF THE INVENTION

Intraoperative control of intraocular infusion pressure is an important parameter in vitreous surgery. Pressure regulation has been accomplished in most part using gravity-fed systems involving the relative height of the infusion bottle above the eye. While this method is relatively controlled, it does not offer the ability to quickly raise the intraoperative pressure for hydraulic reattachment techniques, does not alloy rapid initial injection, and may lead to hypotony because of its limited flow rate. A discussion of the development of gas infusion may be found in "Vitreous Microsurgery" by Steven Charles, M.D. in Williams & Wilkins, 1981, volume 4. As noted therein, there are known power injectors or pumps which are capable of maintaining a more constant intraocular pressure during air infusion. Such devices have also been developed wherein a microcompressor is used to produce an inflow of air dependent upon intraocular pressure. As these advances are made in air infusion apparatus, a need exists for controlled intraocular infusion apparatus which would facilitate the interchangeability of infusion air and an infusion fluid.

SUMMARY OF THE INVENTION

It is an object of the present invention to enable the surgeon to quickly switch from fluid infusion to air infusion.

Yet another object of the invention is to enable the usage of momentary high infusion pressure for such purposes as controlling bleeding during the surgery.

These and other objects and advantages are accomplished in our invention through a novel arrangement of conduits and valves which allow the constant maintenance of the desired intraocular pressure and the flexibility of using either air or fluid infusion. The invention utilizes an infusion bottle as a reservoir for the infusion fluid. A continuous infusion air pump, such as a Grieshaber Air System, may be utilized to pressurize the infusion fluid bottle to the desired infusion pressure. The output of the pump is also used directly to provide pressurized air via a conduit for air infusion. A conduit from the infusion bottle provides pressurized infusion fluid for infusion. The air conduit and fluid conduit are preferentially formed as a dual-tube conduit and are connected to a three-way stopcock which allows the physician to select either air infusion or fluid infusion.

BRIEF DESCRIPTION OF THE DRAWINGS

Apparatus embodying features of our invention are depicted in the appended drawings which form a portion of this invention and wherein.

DESCRIPTION OF A PREFERRED EMBODIMENT

Figure 1:
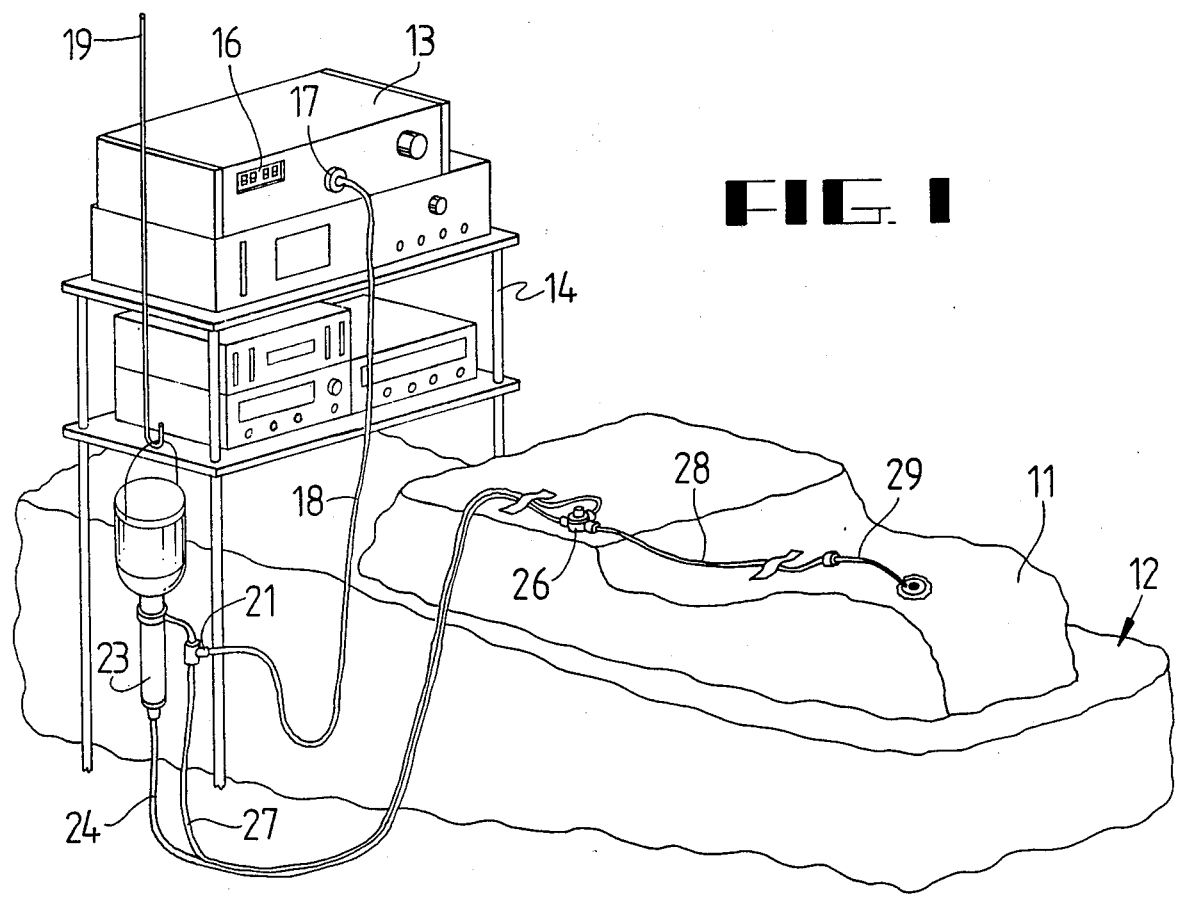
FIG. 1 is a perspective view showing the apparatus as used during surgery.
Figure 2:
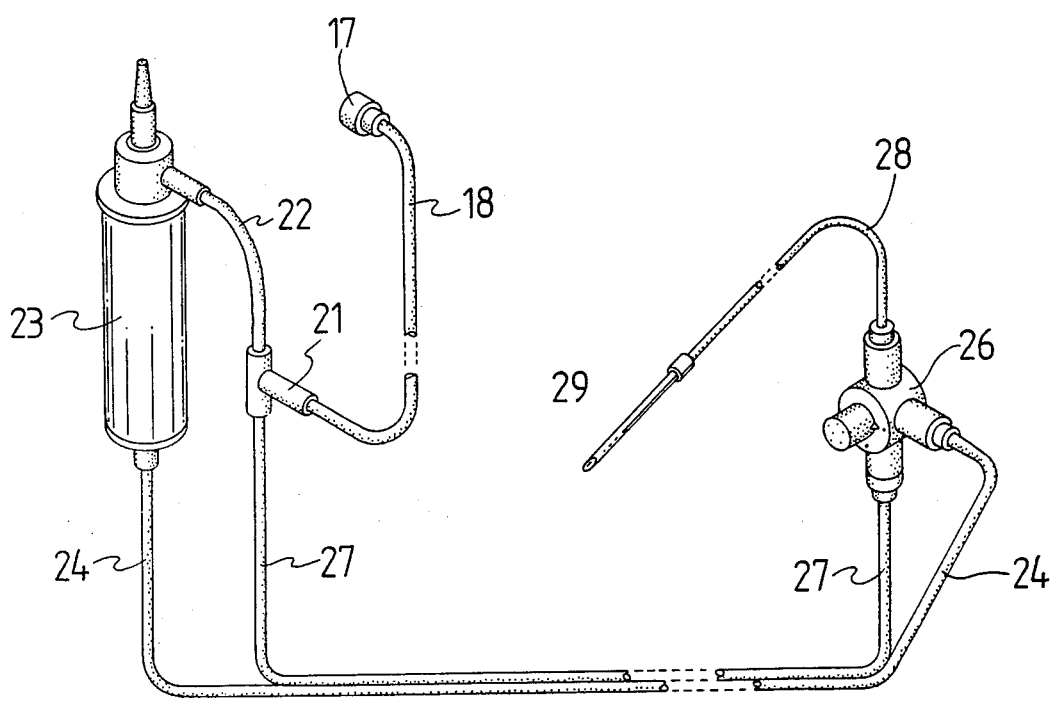
FIG. 2 is a broken lay-out view showing the invention not in use.

Referring to the figures for a better understanding of the invention, it may be seen that the invention is for use with a patient who is lying beneath surgical drapes 11 on an operating table 12. A continuous infusion air pump 13 is located on an equipment stand 14 as is conventional practice. The output of the air pump 13 is displayed as by LED's at a panel 16 so that the pressure generated thereby may be monitored by the surgery team and controlled.

A connector 17 attaches a flexible conduit 18 to the pump 13 in any conventional manner as is well known in the art. The conduit 18 extends from the equipment stand 14 to near an IV support 19 and terminates in a T-connector 21 or other suitable device for directing the airflow from the pump 13 along two paths. A fluid pressurization conduit 22 is connected between the T-connector 21 and an infusion bottle 23 or cylinder supported by the IV support 19 and serves to pressurize the fluid therein in accordance with the output pressure of the pump 13. A fluid delivery conduit 24 is connected as the output of infusion bottle 23 and terminates as one input to a stopcock or valve 26. An air delivery conduit 27 is connected between the remaining branch of the T-connector 21 and the valve 26. The valve 26 has a single output to an infusion conduit 28 which is connected to and supplies an infusion cannula 29.

The infusion bottle 23 is placed at the patient's eye level as shown in FIG. 1 and air is pumped into the bottle 23 via conduits 18 and 22 to provide the desired infusion pressure. Although a normal starting pressure may be selected, it should be clear that the infusion pressure can be rapidly changed by adjusting the output pressure of the air pump 13. The air pump selected should have a digital display 16 of the pressure which should be visible to all operating personnel. It has been determined that the displayed pressure, conduit pressure and intraocular pressure agree to within two to four mm of Hg using the present apparatus.

Valve 26 allows the surgical team to quickly switch from fluid infusion to air infusion. Conduits 24 and 27 may be formed from the two halves of a twin plastic tube, for example Dicoc Twin Bore Silicone IV tubing, such that the valve 26 may be located proximal the cannula 29, thereby minimizing the time required to clear infusion fluid from the system when air is desired.

From the foregoing, it may be seen that we have provided an effective apparatus which greatly improves the surgeon's efficiency in vitreous procedures where fluid to air infusion changes are desired and also provides a readily controllable means for varying the infusion pressure during fluid infusion. As is well known, it is possible to stop bleeding by raising the intraocular pressure to known levels, usually 35 to 45 mm of Hg. Using the present invention with a digital display 16 allows the surgical team to quickly determine the infusion pressure levels and rapidly change the level as required.

While we have shown our invention in one form, it will be obvious to those skilled in the art that it is not so limited but is susceptible of various changes and modifications without departing from the spirit thereof.

What we claim is:

1. Apparatus for use in continuous fluid infusion during vitrectomy in combination with a continuous infusion air pump wherein the infusion pressure is maintained by the output air from said continuous infusion air pump, comprising:
   (a) a continuous infusion air pump;
   (b) first means for supplying air from said continuous infusion air pump to a reservoir for maintaining a fluid other than air at a specified pressure;
   (c) an infusion cannula means for insertion into the eyeball;
   (d) second means for supplying said fluid from said reservoir to said infusion cannula;
   (e) third means for supplying air from said pump to said cannula at said specified pressure to maintain an intraocular pressure at a desired level;
   (f) fourth means for selectively connecting said second or third means to said cannula.

2. Apparatus as defined in claim 1 wherein said reservoir comprises an infusion bottle.

3. Apparatus as defined in claim 1 wherein said first means comprises a conduit member receiving air output by said pump and directing said air to said reservoir, with said reservoir having a limited volume whereby said air and fluid retained therein are subject to equal pressurization.

4. Apparatus as defined in claim 3 wherein said second means comprises a conduit member connected to said reservoir for receiving fluid therefrom and connected to said fourth means.

5. Apparatus as defined in claim 4 wherein said third means comprises a conduit member receiving air from said pump and connected to said fourth means.

6. Apparatus as defined in claim 5 wherein said fourth means comprises a valve having a first inlet connected to said second means and a second inlet connected to said third means and an outlet connected to said cannula such that fluid or air from said second or third means may be selectively supplied to said cannula.

7. Apparatus as defined in claim 6 wherein each of said conduit members comprise a length of flexible silicone tubing.

8. Apparatus as defined in claim 6 wherein said second and third means are formed from twin-bore silicone tubing with one bore serving as a conduit for said fluid and with the other bore serving as a conduit for air.

9. Apparatus as defined in claim 3 wherein said third means comprises a conduit means receiving air from said pump and connected to said fourth means.

10. Apparatus as defined in claim 3 wherein said fourth means comprises a valve having a first inlet connected to said second means and a second inlet connected to said third means and an outlet connected to said cannula such that fluid or air from said second or third means may be selectively supplied to said cannula.

11. Apparatus as defined in claim 3 wherein said second and third means are formed from twin-bore silicone tubing with one bore serving as a conduit for said fluid and with the other bore serving as a conduit for air.

12. Apparatus as defined in claim 1 further comprising means for providing a human sensible indication of the output pressure of said pump.

13. Apparatus for use in continuous fluid infusion during intraocular surgery in combination with a continuous infusion air pump wherein the output of said continuous infusion air pump is used to supply pressurized air comprising:
   (a) a continuous infusion air pump;
   (b) a reservoir of fluid other than air;
   (c) a conduit connecting said continuous infusion air pump and said reservoir such that the fluid in said reservoir is pressurized to a selected pressure determined by the output of said pump;
   (d) an infusion cannula means for insertion into a patient's eye;
   (e) a fluid conduit connected to said reservoir such that fluid from said reservoir may pass therethrough;
   (f) an air conduit connected to said pump such that air may pass therethrough with said air being maintained at said selected pressure;
   (g) means connected to said cannula, said fluid conduit, and said air conduit for selectively allowing air or fluid to pass through said cannula into the interior of the eye such that the intraocular pressure is maintained at said selected pressure.

14. Apparatus as defined in claim 13 wherein said means connected to said cannula comprises a valve connected to said fluid conduit and to said air conduit and connected to said cannula via an output conduit, said valve being adapted to pass air, or fluid to said output conduit.

15. Apparatus as defined in claim 14 wherein each of said conduit members are made from flexible plastic-like material.

16. Apparatus as defined in claim 13 further comprising means for providing a human sensible indication of the output pressure of said pump.

17. A method of regulating fluid infusion pressure during vitrectomy wherein an infusion fluid bottle serves as a reservoir of infusion fluids for an infusion cannula comprising the steps of:
   (a) providing a continuous source of pressurized air;
   (b) pressurizing the fluid in said infusion fluid bottle from said source;
   (c) diverting a portion of said pressurized air from the output of said source to said cannula;
   (d) selecting either said diverted air or said pressurized fluid for infusion via said cannula at a location proximal said cannula.

18. The method as defined in claim 17 further comprising visually displaying the infusion pressure output of said continuous source.

19. The method as defined in claim 18 further comprising varying the intraocular pressure by varying the output pressure of said continuous source.

20. Apparatus for continuous fluid infusion to the interior of the eye during intraocular surgery utilizing an ocular infusion cannula comprising:
   (a) an intraocular cannula;
   (b) pump means for providing a continuous source of pressurized gas at a controlled output pressure;
   (c) means for providing said gas to an infusion bottle for pressurization of an infusion liquid therein;
   (d) means for diverting a portion of said pressurized gas from the output of said pump means to said cannula; and
   (e) means for selecting either pressurized gas from said means for diverting pressurized fluid for infusion via said cannula such that intraocular pressure is maintained substantially at said controlled pressure.

* * * * *